(12) United States Patent
Bradley et al.

(10) Patent No.: US 9,381,022 B2
(45) Date of Patent: Jul. 5, 2016

(54) LABRUM RETRACTING BURR

(71) Applicant: Arthrex, Inc., Naples, FL (US)

(72) Inventors: James P. Bradley, Pittsburgh, PA (US);
Reinhold Schmieding, Naples, FL (US);
Kenneth M. Adams, Naples, FL (US);
Philip S. O'Quinn, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/676,086

(22) Filed: Apr. 1, 2015

(65) Prior Publication Data

US 2015/0201951 A1 Jul. 23, 2015

Related U.S. Application Data

(60) Division of application No. 12/843,560, filed on Jul. 26, 2010, now abandoned, which is a continuation-in-part of application No. 11/518,909, filed on Sep. 12, 2006, now abandoned.

(60) Provisional application No. 60/715,615, filed on Sep. 12, 2005.

(51) Int. Cl.
*A61B 17/00* (2006.01)
*A61B 17/16* (2006.01)
(Continued)

(52) U.S. Cl.
CPC ......... *A61B 17/1615* (2013.01); *A61B 17/1633* (2013.01); *A61B 17/1659* (2013.01); *A61B 17/1684* (2013.01); *A61B 17/32002* (2013.01); *A61B 17/0218* (2013.01); *A61B 17/320758* (2013.01); *A61B 17/3496* (2013.01); *A61B 2017/00473* (2013.01);
(Continued)

(58) Field of Classification Search
CPC . A61B 17/16; A61B 17/1633; A61B 17/1613
USPC ............ 606/79–85, 86 R, 150, 167, 170, 180
See application file for complete search history.

(56) References Cited

U.S. PATENT DOCUMENTS

| 3,126,021 A | 3/1964 | May |
| 4,324,044 A * | 4/1982 | Shahinian, Jr. .. A61B 17/32093 30/294 |

(Continued)

FOREIGN PATENT DOCUMENTS

| WO | WO 01/50965 A2 | 7/2001 |
| WO | WO 03/024340 A2 | 3/2003 |

(Continued)

OTHER PUBLICATIONS

E. S. Araujo et al., "Effects of gamma-irradiation on some properties of durolon polycarbonate", Radiation Physics and Chemistry, Jan. 1, 1999, pp. 79-84, vol. 53, Issue 1.

*Primary Examiner* — Matthew Lawson
(74) *Attorney, Agent, or Firm* — Blank Rome LLP

(57) ABSTRACT

A rotary abrader allowing for improved visibility during surgery and improved aspiration of waste material. This is accomplished by providing a hood or sheath formed of a clear material and available in various shapes and sizes. The clear hood or sheath is also provided with a flattened, angled portion at a tip of the hood, to assist with retraction of the labral tissue while burring the glenoid rim. Slots are provided on the cannulated tube to provide aspiration of waste material and used to attach the hood to the cannulated tube.

4 Claims, 13 Drawing Sheets

(51) Int. Cl.
*A61B 17/32* (2006.01)
*A61B 17/02* (2006.01)
*A61B 17/3207* (2006.01)
*A61B 17/34* (2006.01)
*A61B 17/22* (2006.01)
*A61B 17/17* (2006.01)

(52) U.S. Cl.
CPC ............... *A61B 2017/00902* (2013.01); *A61B 2017/00907* (2013.01); *A61B 2017/1602* (2013.01); *A61B 2017/1778* (2013.01); *A61B 2017/22079* (2013.01); *A61B 2017/320004* (2013.01); *A61B 2217/005* (2013.01); *Y10T 29/49826* (2015.01)

(56) References Cited

U.S. PATENT DOCUMENTS

| | | | |
|---|---|---|---|
| 4,872,452 A * | 10/1989 | Alexson | A61B 17/1659 30/276 |
| 4,923,462 A | 5/1990 | Stevens | |
| 4,950,238 A | 8/1990 | Sullivan | |
| 5,234,436 A * | 8/1993 | Eaton | A61B 17/320016 30/151 |
| 5,507,765 A * | 4/1996 | Mott | A61B 10/02 600/567 |
| 5,540,708 A * | 7/1996 | Lim | A61B 17/32002 30/240 |
| 5,674,237 A * | 10/1997 | Ott | A61B 17/3496 604/264 |
| 5,681,328 A * | 10/1997 | Lamport | A61B 17/12013 606/140 |
| 5,794,915 A | 8/1998 | Shimizu et al. | |
| 5,913,867 A | 6/1999 | Dion | |
| 6,053,923 A * | 4/2000 | Veca | A61B 17/32002 606/79 |
| 6,214,009 B1 * | 4/2001 | Toriumi | A61B 17/32002 606/80 |
| 6,511,493 B1 | 1/2003 | Moutafis et al. | |
| 6,610,059 B1 | 8/2003 | West, Jr. | |
| 7,118,574 B2 | 10/2006 | Patel et al. | |
| 7,585,300 B2 | 9/2009 | Cha | |
| 2003/0078586 A1 | 4/2003 | Shapira | |
| 2004/0181251 A1 * | 9/2004 | Hacker | A61B 17/32002 606/170 |
| 2005/0054972 A1 * | 3/2005 | Adams | A61B 17/1688 604/22 |
| 2005/0165420 A1 | 7/2005 | Cha | |
| 2006/0085019 A1 * | 4/2006 | Cote | A61B 17/3211 606/167 |
| 2006/0217751 A1 | 9/2006 | O'Quinn et al. | |
| 2007/0060936 A1 * | 3/2007 | Benavitz | A61B 17/1633 606/180 |

FOREIGN PATENT DOCUMENTS

| | | |
|---|---|---|
| WO | WO 2004/093924 A2 | 11/2004 |
| WO | WO 2005/062827 A2 | 7/2005 |

* cited by examiner

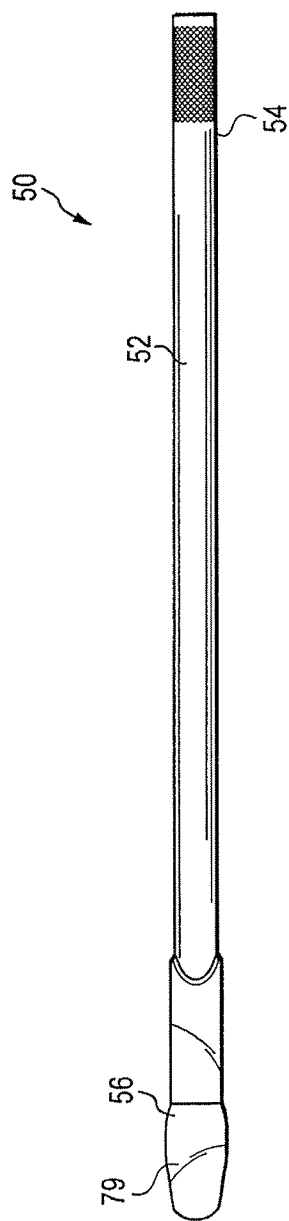
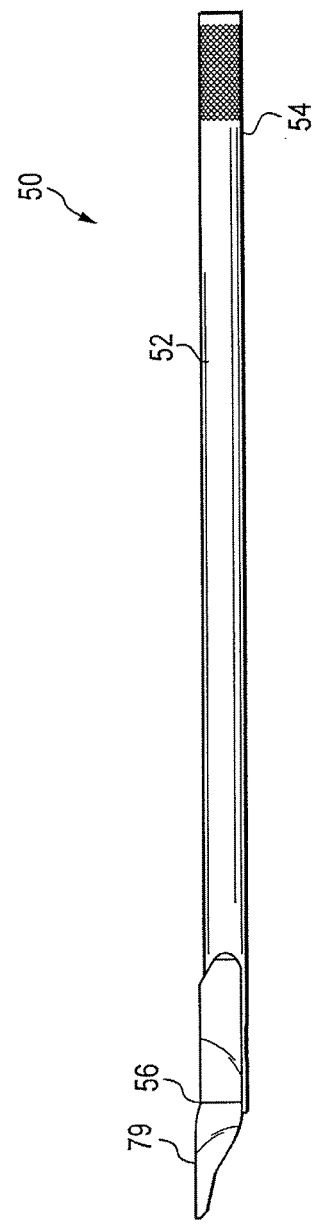
FIG. 1
FIG. 2

SECTION A-A

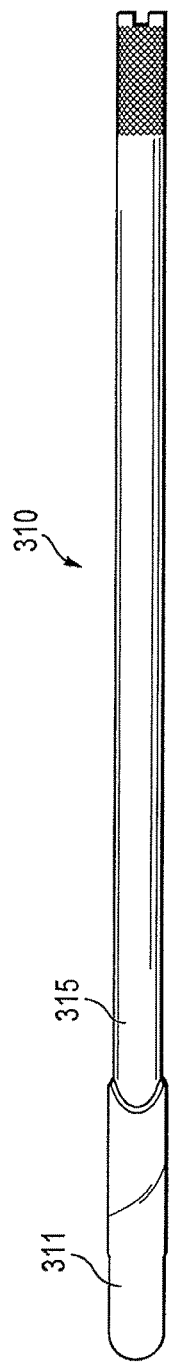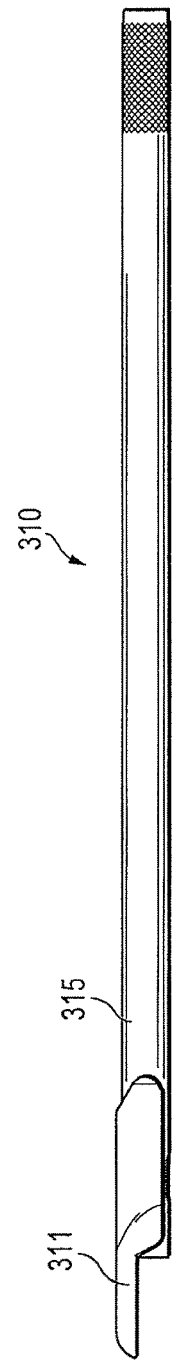

LABRUM RETRACTING BURR

CROSS-REFERENCE TO RELATED APPLICATIONS

This is a divisional of U.S. application Ser. No. 12/843,560, filed Jul. 26, 2010, which is a continuation-in-part of U.S. application Ser. No. 11/518,909, filed Sep. 12, 2006, now abandoned, which in turn claims the benefit of U.S. Provisional Application No. 60/715,615, filed Sep. 12, 2005, the disclosures of which are incorporated by reference in their entirety herein.

FIELD OF THE INVENTION

The present invention relates to rotary abraders used in surgery and, more particularly, to an abrader which gives the surgeon an improved view of the surgical site during arthroscopic procedures.

BACKGROUND OF THE INVENTION

Least invasive surgical techniques have gained significant popularity because of their ability to accomplish outcomes with reduced patient pain and accelerated return of the patient to normal activities. Arthroscopic surgery, in which the intra-articular space is filled with fluid, allows orthopedists to efficiently perform procedures using special purpose instruments designed specifically for arthroscopists. Among these special purpose tools are various manual graspers and biters, electrosurgical devices, and powered shaver blades and rotary abraders. Shaver blades having hollow bores are typically removably coupled to a shaver handpiece and are used for cutting, resecting, boring, and abrading both soft and hard tissue at the surgical site. An arthroscopic abrader (also known as a burr) generally includes a rotatable inner tube having an abrading head at its distal end and fixed outer tube for rotatably receiving the inner tube. Abraders are used for abrading or shaping both soft and hard tissue as bone, cartilage, ligaments, etc. by use of the rotating abrading head. As the tissue is being abraded, debris and fluid are generally drawn or sucked through the rotatable inner shaft which supports the burr.

Requirements for a rotary abrader for arthroscopy include a compact size so as to fit through small cannulae, a means for removal of debris, and a configuration which allows the surgeon to access, while retaining good visibility, structures within a joint. One requirement for good visibility is the effective removal of debris as it is generated. Another is that the instrument be configured so that the view of the active portion of the abrader in contact with the tissue and the view of the tissue being abraded are not obscured by the instrument.

Rotary abraders for arthroscopy generally have a shield, also called a "hood," on one side of the distal end of the outer tube to prevent inadvertent damage to tissue in close proximity to the tissue being abraded. The distal end of this hood is angled with respect to the tube axis so as to expose only one side of the burr head. During use, the burr head (the abrading element at the distal end of the rotating inner member) is subjected to significant lateral forces. Although rotary abraders typically have a bearing near the distal end of the instrument to support the inner member, lateral deflection of the burr head occurs to some degree. Contact between the burr head and the hood is undesirable since the burr will abrade metal from the hood and deposit metallic debris in the joint. Accordingly, it is necessary to leave adequate clearance between the hood and the burr head. Further, hoods are usually opaque, which hinder visibility of the surgical site during surgery.

Removal of debris from the field is accomplished by aspirating the material from the joint via a lumen in the inner, rotating member which is connected through a means in the handpiece to an external vacuum source. The aspiration of material through the inner member is desirable as this allows easy transfer of the materials from the proximal end of the instrument to the aspiration passage of the handpiece. The manner in which material and fluid enter the lumen at the distal end of the instrument has a large effect on the volume of flow through the instrument and on the frequency with which the instrument clogs. Insufficient flow causes decreased visibility because of residual debris suspended in the intra-articular fluid. Clogging requires that the instrument be removed from the joint and "de-clogged." The degree of difficulty of clog removal is determined by the instrument design. Even if clog removal is easily accomplished, removing, de-clogging and reinserting the instrument is a nuisance and causes increased procedure times. Aspiration effectiveness, and therefore instrument design, have a large effect on burr efficiency.

There is a need for an improved rotary abrader that provides a clear hood to improve visibility during surgery.

It is accordingly an object of this invention to produce a rotary abrader with a hood or sheath or guard that is available in various shapes to improve the procedure of abrading tissue.

Further, there is a need for an abrading instrument having rigidity, and an aspiration means which effectively removes debris without clogging and which can be readily cleared of clogs without disassembly, and which enhances surgeon visibility in procedures where visibility is crucial, such as SLAP repair.

SUMMARY OF THE INVENTION

The present invention is a rotary abrader having a clear sheath or hood over the abrading element or burr. Slots provided on the cannulated shaft supporting the burr provide aspiration and are used to attach the hood to the cannulated shaft.

Several hoods in various shapes are provided to cover the burr at the distal end of the abrader. The hoods are formed of a clear material, such as polycarbonate. The clear material of the hoods provide visibility of the burr during the procedures.

The present invention also provides a burr with a hood having a special configuration designed for labrum retracting applications. The hood is preferably formed of a clear material to allow increased visibility of the burr during the labrum retracting and the cutting procedures.

Other features and advantages of the present invention will become apparent from the following detailed description of the invention, which is provided with reference to the accompanying drawings.

BRIEF DESCRIPTION OF THE DRAWINGS

FIG. 1 is a plan view of the outer tube of a rotary abrader in accordance with an embodiment of the invention.

FIG. 2 is a side elevational view of an outer tube of the rotary abrader of FIG. 1.

FIG. 19 is a plan view of an outer tube assembly of a rotary abrader in accordance with another embodiment of the invention.

FIG. 20 is a side elevational view of an outer tube assembly of the rotary abrader of FIG. 19.

DETAILED DESCRIPTION OF THE INVENTION

Figure 3:
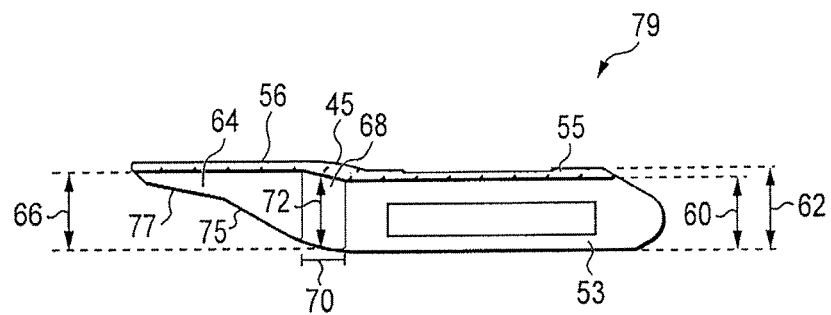
FIG. 3 is a side elevational view of the hood of an outer tube assembly of the rotary abrader of FIG. 1.
Figure 4:
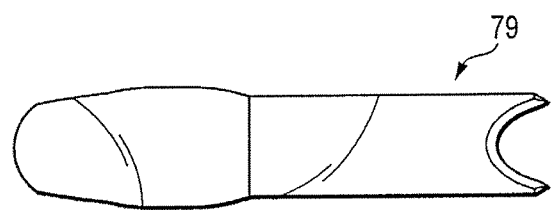
FIG. 4 is a plan view of the hood of an outer tube assembly of the rotary abrader of FIG. 1.
Figure 5:
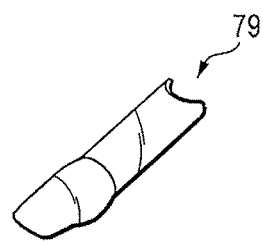
FIG. 5 is a perspective view of the hood of the outer tube assembly of the rotary abrader of FIG. 1.
Figure 6:
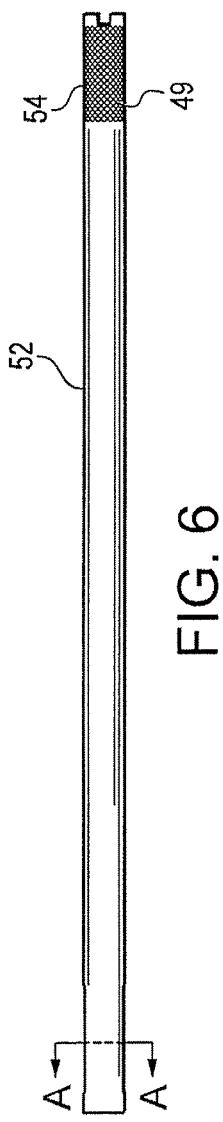
FIG. 6 is a plan view of the outer tube of the rotary abrader of FIG. 1.
Figure 7:
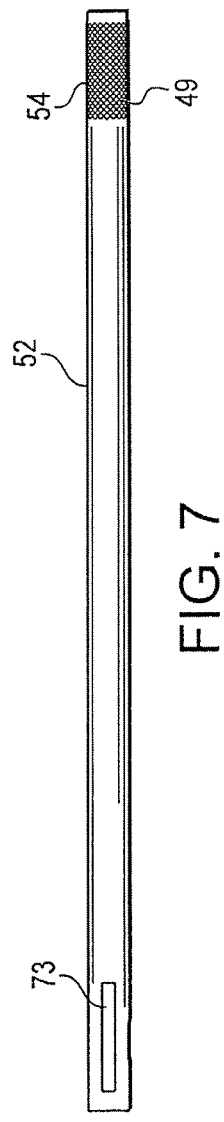
FIG. 7 is a plan view of the outer tube of the rotary abrader of FIG. 1.
Figure 8:
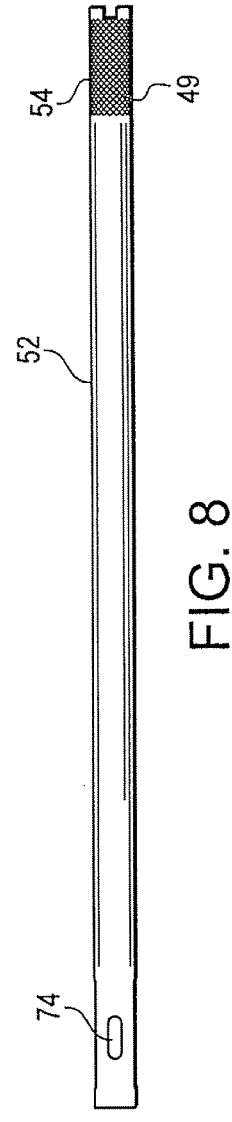
FIG. 8 is a plan view of the outer tube of the rotary abrader of FIG. 1.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Referring now to the drawings, where like elements are designated by like reference numerals, FIGS. 1 through 5 illustrate the outer tubular portion 50 of a rotary abrader formed in accordance with the first embodiment of the invention. Outer tube 52 has a proximal end 54 and a distal end 56. Tube 52 has a lumen 53 of diameter 60 and an outer diameter 62. Distal end 56 has a first portion 64 with an inner diameter 66 formed therein, and a second portion 68 of length 70 with a diameter 72 formed therein. Diameter 72 decreases slightly and varies at slope 45 at distal end 56. Diameter 72 is slightly larger than diameter 60. Diameter 66 is slightly larger than diameter 72. Beveled surfaces 75 and 77 together with outer surfaces 55 define a hood (or guard) 79.

The hood 79 may be formed of any material, but in an exemplary embodiment, at least a portion of hood 79 is made of a clear polymer plastic material, such as polycarbonate. The polycarbonate hood 79 enhances visualization of the operational site. The hood 79 also is provided to enhance aspiration and to protect tissue surrounding the operational site.

Figure 9:
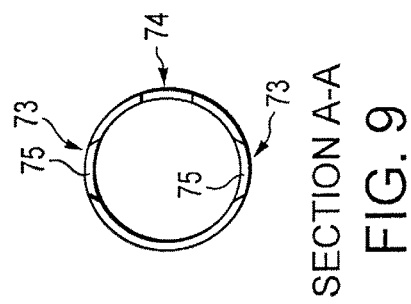
FIG. 9 is an expanded axial view of the objects at location A-A of FIG. 6.
Figure 10:
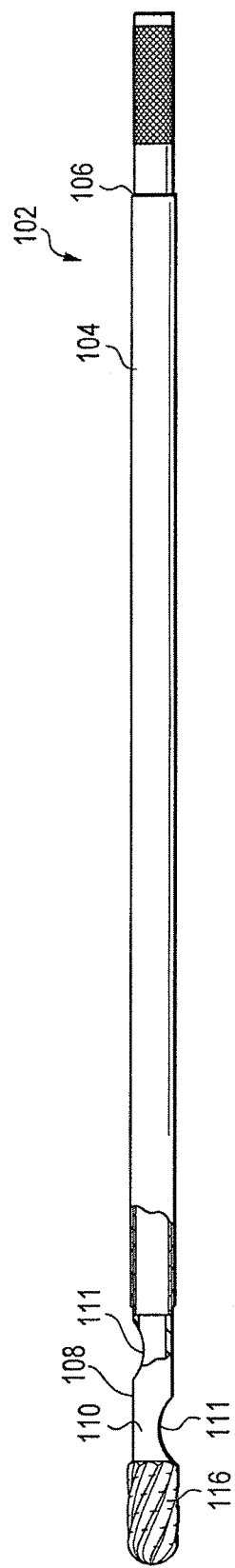
FIG. 10 is a plan view of the inner tube assembly of the rotary abrader.

The outer tube 52, as illustrated in FIGS. 6 through 9, is preferably about 5.15 inches long and has a diameter of about 0.171 inches. Further, elongated slots 73 and 74 extend from the lumen 53 to the tube outer surface 55 (FIG. 3). Two elongated slots 73 are used to attach hood 79 to the outer tube 52. As shown in FIG. 9, slots 73 have inward bevels for insert molding, created by laser cutting, to allow the plastic from hood 79 to fill the space 75. Also, the slots 73, having a dovetail configuration, prevent the hood 79 from becoming dislodged. A core pin is inserted into the lumen of the outer tube 52 to prevent plastic from obstructing the pathway for inner tube 102 (FIG. 10). Slot 74 provides aspiration of debris and waste without clogging. A raised diamond knurl 49 at the proximal end 54 of the outer tube 52 is a point of attachment for the outer tube 52 with the inner tube 102 (FIG. 10).

Figure 12:
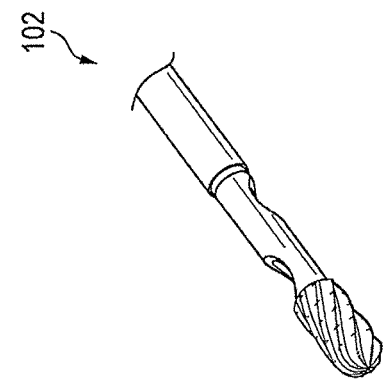
FIG. 12 is a perspective view of the distal end of the inner tube assembly of the rotary abrader.
Figure 11:
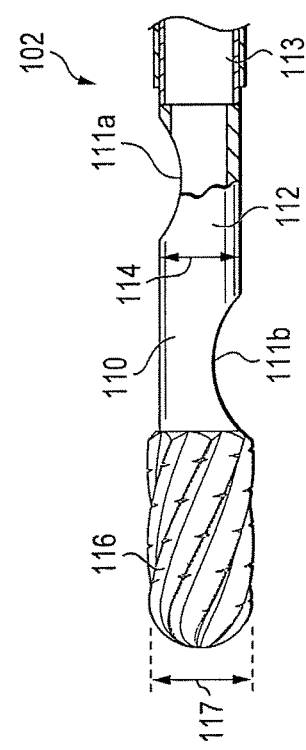
FIG. 11 is an expanded plan view of the distal end of the inner tube assembly of the rotary abrader.
Figure 13:
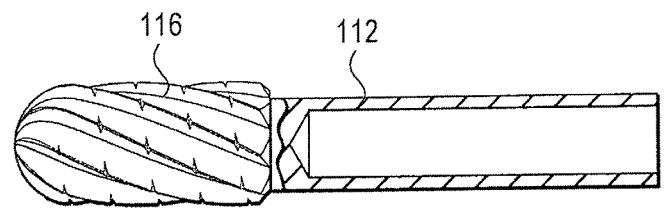
FIG. 13 is an expanded plan view of the distal end of the inner tube assembly of a rotary abrader in accordance with another embodiment of the invention.
Figure 14:
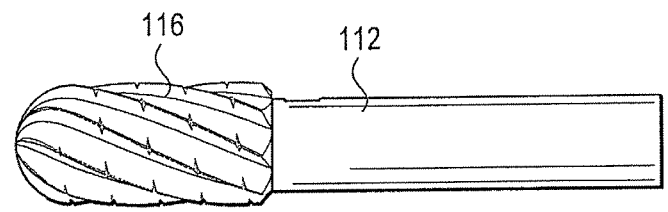
FIG. 14 is an expanded plan view of the distal end of the inner tube assembly of a rotary abrader in accordance with another embodiment of the invention.
Figure 15:
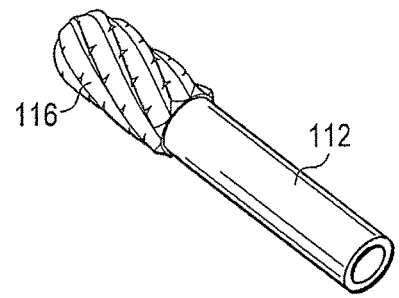
FIG. 15 is a perspective view of the distal end of the inner tube assembly of a rotary abrader in accordance with another embodiment of the invention.
Figure 16:
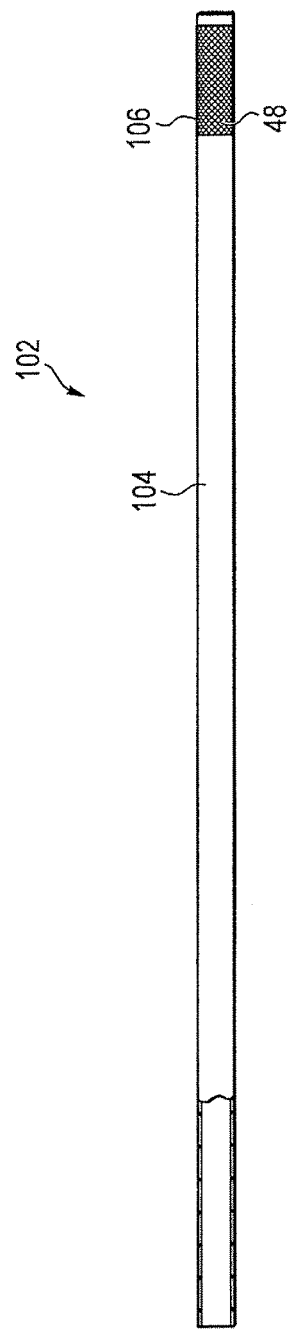
FIG. 16 is a plan view of the inner tube of a rotary abrader.

Referring now to FIGS. 10 through 12, inner tube assembly 102 of a rotary abrader constructed in accordance with the principles of the invention has an elongated tubular portion 104 with a proximal end 106 and a distal end 108. Distal end 108 has affixed thereto portion 110 having a diameter 114, and a distal portion 116 forming an abrading element (or burr head) of diameter 117. In addition, a Teflon (FEP) shrink tubing covers the elongated tubular portion of inner tube assembly 102 to prevent wear and keep the inner and outer tubes more concentric. Near distal end 108 of tubular portion 104 aspiration port 111a extends from lumen 112 to outer surface 113. Aspiration port 111b extends from the distal portion 116 to a distance immediately before 111a. The suction pathways 111a and 111b enhance aspiration of waste and debris. An example of a surgical abrader that provides a suction port proximal to the bearing to enhance aspiration is disclosed in U.S. Pat. No. 7,077,845, which is incorporated herein by reference in its entirety. In another preferred embodiment, as illustrated in FIGS. 13 through 15, the burr head and portion 112 extends about 1 inch without aspiration ports at the distal portion 116. The aspiration ports may be disposed on the inner tube a distance away from the burr head. In addition, as best seen in FIG. 16, the inner tube 102 has an elongated tubular portion 104 that extends about 5.4 inches. A raised diamond knurl 48 at the proximal end 106 of the inner tube 102 is a point of attachment for the inner tube 102 with the outer tube 52 (FIG. 1).

Figure 17:
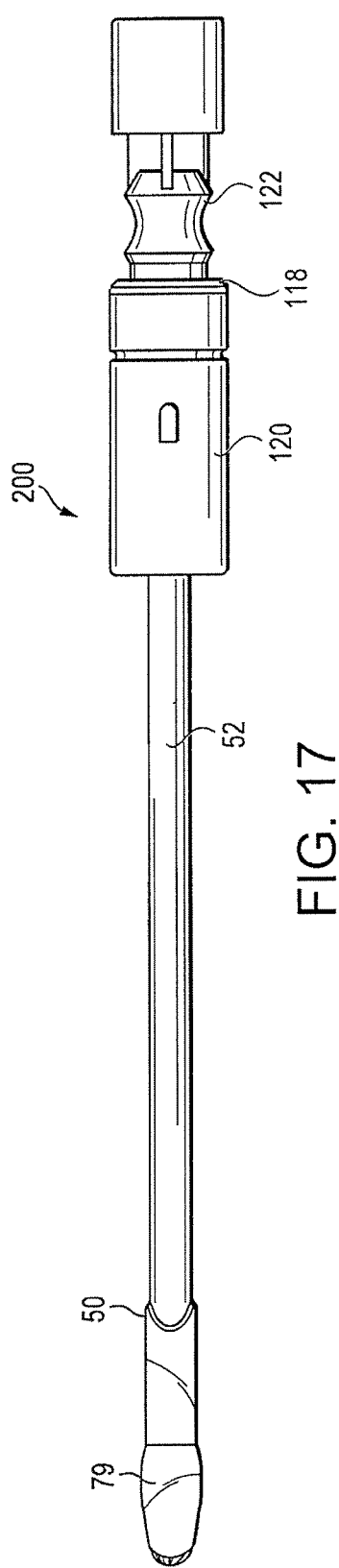
FIG. 17 is a plan view of the assembled rotary abrader.
Figure 18:
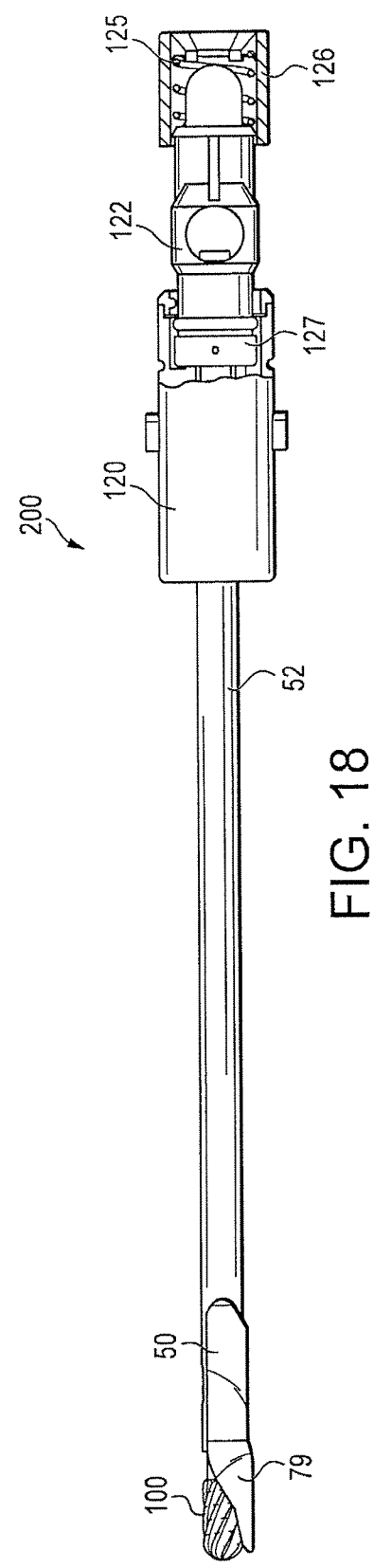
FIG. 18 is a side elevational view of an assembled rotary abrader.
Figure 21:
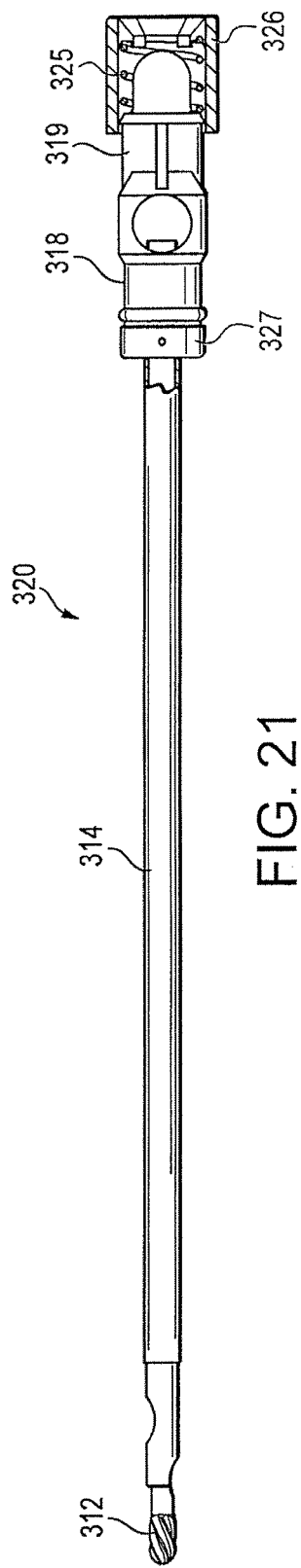
FIG. 21 is a plan view of an inner tube assembly of a rotary abrader.
Figure 22:
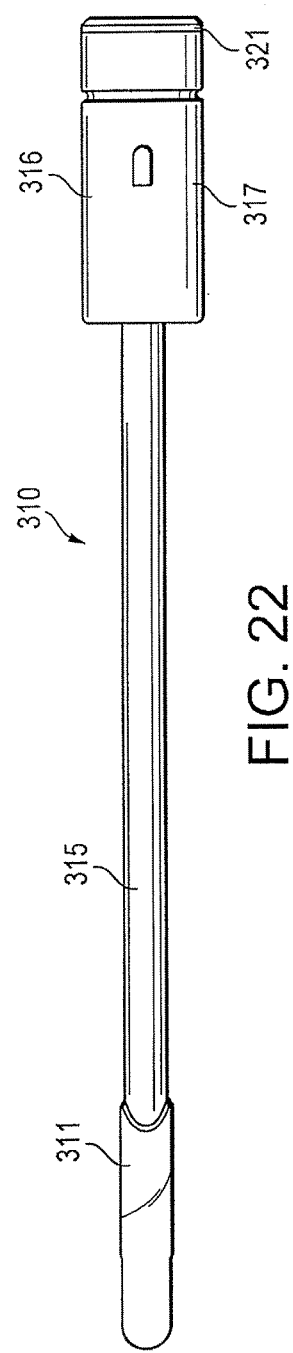
FIG. 22 is a plan view of an outer tube assembly of the rotary abrader of FIG. 19.

Referring now to FIGS. 17 and 18, an assembled rotary abrader 200 is shown. To assemble, an inner tube assembly 100 is inserted into the outer tube 52 of outer assembly 50. Inner hub 122 is inserted into the outer hub 120, which is held secure by a retaining ring 118. The inner hub 122 of inner tube assembly 100, includes a spring 125, spring retainer 126, and thrust washer 127. Also, the clear tip hood 79 covers the burr blade.

In another embodiment, the clear tip hood is removably interchangeable with other hoods, which are provided in various shapes. U.S. patent application Ser. No. 11/365,939, which is incorporated herein by reference in its entirety, provides another embodiment of an endoscopic rotary abrader with an abrader and an outer assembly portion having flush ends and a removable hood.

In another preferred embodiment, as illustrated in FIGS. 19 through 25, a rotary abrader has an outer assembly 310 and inner assembly 320. A hood 311 is insert molded onto the outer tube 315. The hood 311 covers the burr blade 312. This abrader is known as a SLAP burr. In this embodiment, the inner tube 314 is removable from the outer tube 315. The outer assembly 310 has a proximal end 316 with a hub 317 affixed to the proximal end 316 of outer tube 315. The inner assembly 320 has a proximal end 318 with a hub 319 affixed to the proximal end 318 of inner tube 314. As discussed above, to assemble the rotary abrader, the inner tube assembly 320 is inserted into the outer tube 315 of outer assembly 310. Inner hub 319 is inserted into the outer hub 317, which is held secure by a retaining ring 321. The inner hub 319 of inner tube assembly 320, includes a spring 325, spring retainer 326, and thrust washer 327.

Figure 23:
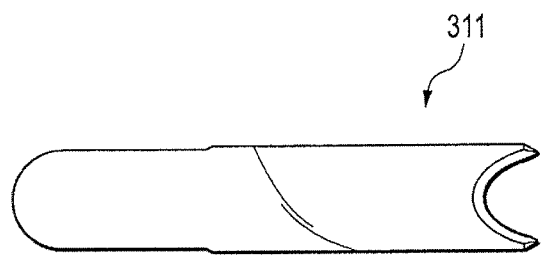
FIG. 23 is a plan view of a hood of the rotary abrader of FIG. 19.
Figure 24:
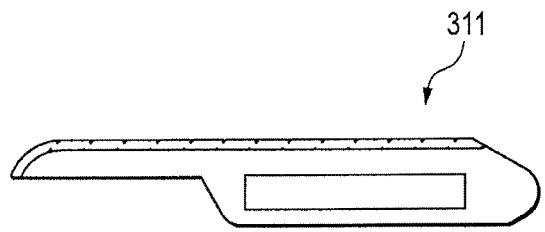
FIG. 24 is a side elevational view of the hood of a rotary abrader of FIG. 19.
Figure 25:
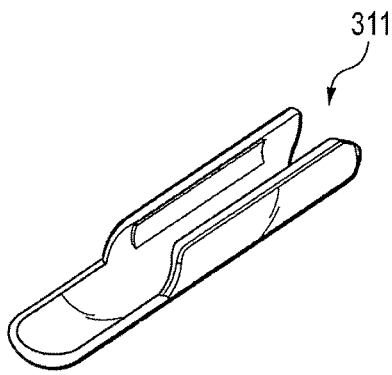
FIG. 25 is a perspective view of a hood of the rotary abrader of FIG. 19.

As best seen in FIGS. 23 through 25, the hood 311 has a different shape than the embodiment discussed above. This shape provides better protection for the surrounding tissue as the burr blade abrades the tissue. The hood is preferably made of a polycarbonate or other clear material to enhance visibility of the surgical site. Although the hood is shaped differently than the embodiments described above, the abrader still maintains the required minimum clearance between the burr head and the hood and does not obstruct the surgeon's view. In a preferred embodiment, the hood is enlarged as compared to the diameter of the outer tube. In this embodiment, the diameter of the abrading element can be increased and still maintain the minimum clearance required between the element and the hood.

Figure 26:
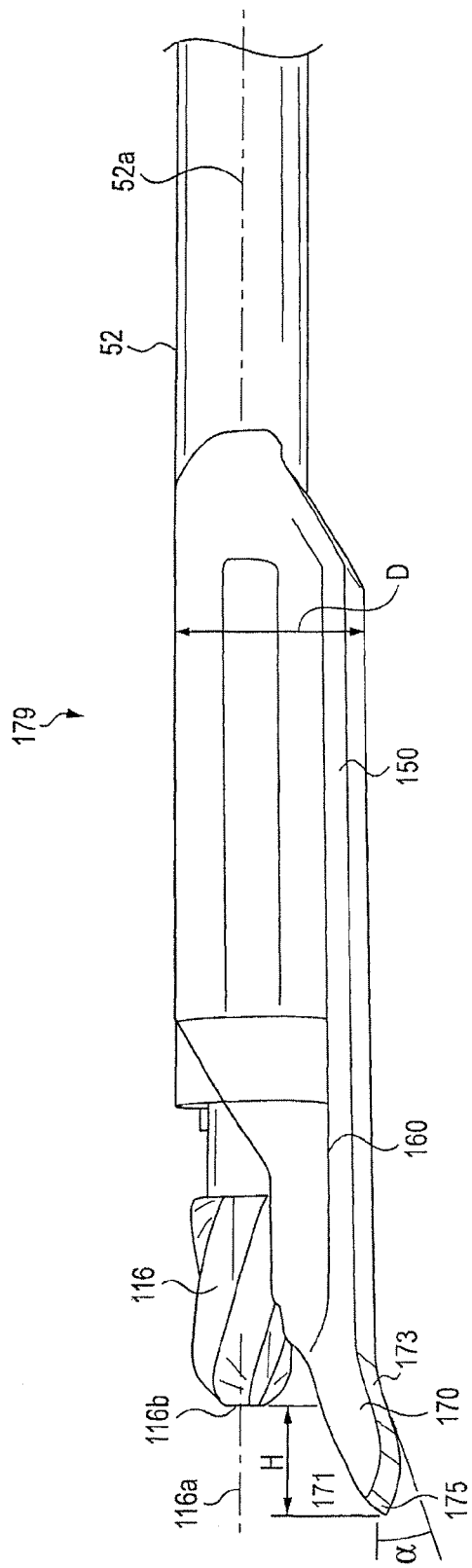
FIG. 26 is a side view of a distal end of a rotary abrader with a hood according to another embodiment of the present invention.
Figure 27:
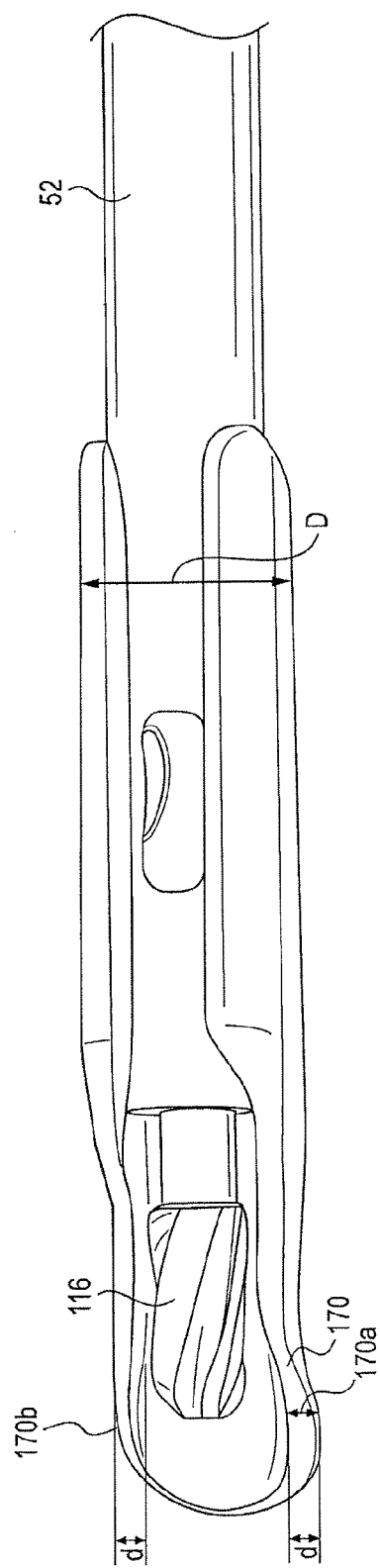
FIG. 27 is another side view of the distal end of the rotary abrader of FIG. 26, rotated about 90 degrees.
Figure 28:
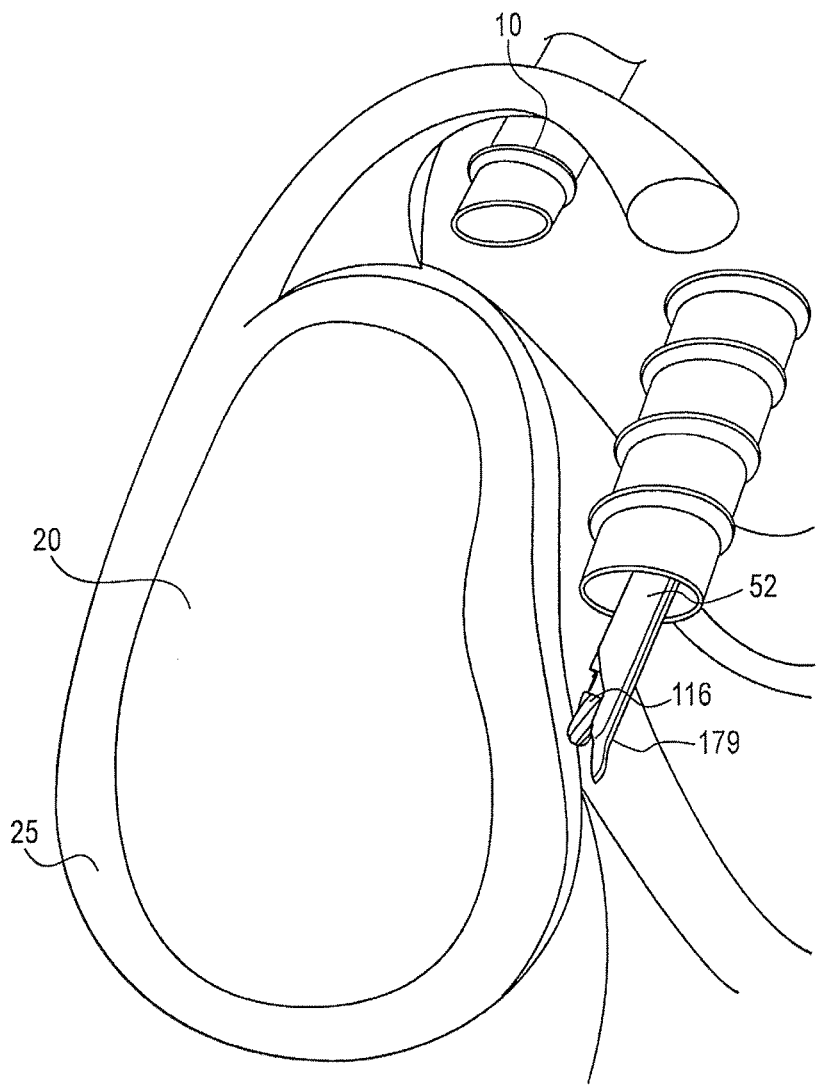
FIG. 28 is a lateral view of a human shoulder with the glenoid and labrum undergoing an exemplary method of glenoid repair with the rotary abrader and hood of the present invention.

FIGS. 26-28 illustrate another embodiment of a hood (guard) 179 of the present invention which may be employed in lieu of the hoods 79, 311 (and with the rotary cutters of the above-described embodiments, for example, with the burr 116 of rotary abrader 200).

Hood 179 is also formed of a clear material but is provided with a specific design and configuration which allows the instrument to be employed both for tissue retracting (for example, labrum retracting in a labral repair) and cutting of tissue (for example, burring of the glenoid rim during the labral repair). As detailed below, the hood is provided with a distal portion having a flatter and wider profile than the rest of the hood, and forming an angle with the central axis of the burr. Preferably, the hood 179 is employed for simultaneously retracting the labrum and cutting of the glenoid rim during a labral repair procedure.

Hood 179 may be removably attached to the outer tube 52 of outer assembly 50 of the rotary abrader 200, or may be removably interchangeable with other hoods, which are provided in various shapes and dimensions, as detailed in U.S. Patent Application Publication No. 2006/0217751, the disclosure of which is incorporated herein by reference in its entirety.

Hood 179 is provided with a substantially cylindrical, proximal body portion 150 adjacent a middle portion 160 which in turn continues with an angled, flattened distal portion 170 provided at the tip of the hood. Angled, flattened distal portion 170 extends above a most distal end 116b of rotary element 116 (burr 116) by a distance "H" of about 3-20 mm, more preferably of about 10 mm (as shown in FIG. 26).

Distal portion 170 is provided with top and bottom surfaces 171, 173 that may taper in width distally and terminate at an end 175, as shown in FIG. 26. End 175 is preferably a blunt end to avoid cutting or piercing of tissue during tissue retracting. Top and bottom surfaces 171, 173 may be slightly curved or may be flattened. Distal portion 170 is also provided with side areas 170a, 170b that flare out a distance "d" from the outer diameter "D" (FIGS. 26 and 27) of proximal body portion 150, as shown in FIG. 27, to increase the contact area with the tissue to be retracted (i.e., with the labrum to be retracted). Distance "d" may be about 0.5-5 mm, more preferably about 2 mm.

While cylindrical body portion 150 and middle portion 160 extend about parallel to longitudinal axis 52a of the outer tube 52 and also to longitudinal axis 116a of the burr 116, the distal portion 170 forms an angle α (of about 10-60 degrees, more preferably of about 30 degrees) with the longitudinal axis 52a of the outer tube 52 and the longitudinal axis 116a of the burr 116, as best shown in FIG. 26. In this manner, hood 179 acts as a retractor that moves the tissue (labrum) away from the burr head 116, to keep it safe during the cutting procedure of the glenoid rim (i.e., during the glenoid burring part of the labral repair procedure).

Hood 179 may be formed of any material, but in an exemplary embodiment, at least a portion of hood 179 (for example, distal portion 170) is made of a clear polymer plastic material, such as polycarbonate. The polycarbonate hood 179 enhances visualization of the operational site. The hood 179 also is provided to enhance aspiration and to protect tissue surrounding the operational site, by retracting tissue.

Slots may be also provided on the cannulated tube to provide aspiration of waste material and used to attach the hood 179 to the cannulated tube (as detailed in the above-described embodiments). The slots may be provided in different shapes (for example, a dovetail configuration) to prevent the hood 179 from becoming dislodged.

The hood 179 of the present invention may be employed in a method of treatment of tissue, such as retraction of soft tissue from bone during shaping of the bone. In an exemplary embodiment only, the method of tissue treatment of the present invention comprises the steps of: (i) providing clear hood 179 attached to a cutting instrument in the proximity of a first tissue adjacent a second tissue (for example, soft tissue attached to bone); and (ii) retracting the first tissue with the clear hood 179 while simultaneously cutting or shaping the second tissue (for example, the bone) with the cutting instrument.

The hood 179 of the present invention may be also employed in a labral repair procedure such as an arthroscopic repair of a SLAP lesion by: (i) providing clear hood 179 attached to a rotary cutter in the proximity of the glenoid labrum; (ii) retracting the glenoid labrum with the clear hood; and (iii) cutting or shaping the glenoid rim with the rotary cutter. Preferably, steps (ii) and (iii) are conducted simultaneously.

FIG. 28 illustrates the interior of a right human shoulder in a lateral perspective with glenoid 20 and glenoidal labrum 25 undergoing an exemplary method of glenoid repair (such as an arthroscopic repair of type II SLAP (superior labrum anterior-posterior) lesion or glenoid resurfacing) with the hood 179 and burr 116 of a rotary abrader such as rotary abrader 200 of the present invention.

Appropriate radiological studies may be conducted to determine if the humeral head and/or glenoid 20 have advanced patterns of wear that may require procedures alternative or additional to the one of the present invention. The method of glenoid repair of the present invention may be performed in the lateral decubitus or beach chair position. The arthroscope is initially inserted into the glenohumeral joint through a posterior portal.

Once the complete visualization of the glenoid is established, the rotary abrader 200 (with the hood 179) is introduced through cannula 10 or through an anterior portal, as shown in FIG. 28. While the distal end 170 of the hood 179 retracts glenoid labrum 25, burr 116 shapes the glenoid surface (to remove remaining articular cartilage, or to remove the damaged cartilage and bone). While the glenoid adjacent to the labrum is cut/shaped, the hood 179 preserves the labral tissue that remains intact, as it could be utilized to assist in additional procedures (such as fixation of an allograft to the glenoid).

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed as new and desired to be protected by Letters Patent of the United States is:

1. A method of attaching a plastic hood to a metal tip of a rotary abrader, the method comprising the steps of:
    providing a rotary abrader with an inner tube rotatably positioned within an outer tube, and an abrader element located at a distal end of the inner tube, wherein the outer tube is provided with a metal tip at a distal end of the outer tube, the metal tip having a plurality of elongated slots extending from a lumen of the outer tube to an outer surface of the outer tube; and
    attaching a hood formed of plastic material to the metal tip by injection molding, to allow plastic material from the hood to fill spaces of the plurality of elongated slots of the metal tip, to prevent the hood from becoming dislodged from the metal tip, and to enhance vizualization at a surgical site undergoing abrading with the abrader element of the rotary abrader.

2. The method of claim 1, wherein the plurality of elongated slots are formed by laser cutting.

3. The method of claim 1, wherein the plastic material of the hood is a clear polymeric plastic material.

4. The method of claim 3, wherein the clear polymeric plastic material is polycarbonate.

\* \* \* \* \*